United States Patent
Toro Restrepo et al.

(10) Patent No.: US 10,470,467 B2
(45) Date of Patent: Nov. 12, 2019

(54) **METHOD OF PRODUCTION OF EXTRACT DERIVED FROM *SWINGLEA GLUTINOSA* LEAVES**

(71) Applicant: GOWAN CROP PROTECTION LIMITED, Reading, Berkshire (GB)

(72) Inventors: Jaime Toro Restrepo, Medellin (CO); Sandra Patricia Zapata Rojas, Medellin (CO); James Alberto Jiménez Martinez, Medellin (CO)

(73) Assignee: GOWAN CROP PROTECTION LIMITED, Reading (GB)

( * ) Notice: Subject to any disclaimer, the term of this patent is extended or adjusted under 35 U.S.C. 154(b) by 642 days.

(21) Appl. No.: 15/056,303

(22) Filed: Feb. 29, 2016

(65) Prior Publication Data
US 2016/0278389 A1    Sep. 29, 2016

Related U.S. Application Data

(63) Continuation of application No. 12/466,801, filed on May 15, 2009, now abandoned.

(51) Int. Cl.
| | | |
|---|---|---|
| *A61K 36/75* | (2006.01) | |
| *A61K 36/53* | (2006.01) | |
| *A61K 36/752* | (2006.01) | |
| *A61K 36/61* | (2006.01) | |
| *A01N 65/36* | (2009.01) | |
| *A01N 65/00* | (2009.01) | |

(52) U.S. Cl.
CPC ............. *A01N 65/36* (2013.01); *A01N 65/00* (2013.01); *A61K 36/75* (2013.01)

(58) Field of Classification Search
CPC ...... A61K 36/75; A61K 36/53; A61K 36/752; A61K 36/61
USPC ................................ 424/736, 774, 739, 742
See application file for complete search history.

(56) References Cited

U.S. PATENT DOCUMENTS

| | | |
|---|---|---|
| 5,389,662 A | 2/1995 | Pap et al. |
| 5,498,624 A | 3/1996 | McLoughlin et al. |
| 5,948,805 A | 9/1999 | Geddens et al. |
| 7,297,349 B2 | 11/2007 | Arimoto et al. |
| 8,932,654 B2 | 1/2015 | Martinez |
| 8,993,011 B2 | 3/2015 | Martinez |
| 2002/0031538 A1 | 3/2002 | Scarmoutzos |
| 2010/0316751 A1 | 12/2010 | Jimenez Martinez et al. |
| 2011/0020481 A1 | 1/2011 | Jimenez Martinez |
| 2011/0059195 A1 | 3/2011 | Martinez |

FOREIGN PATENT DOCUMENTS

WO    WO 2010/131109 A1    11/2010

OTHER PUBLICATIONS

Alvarez et al. ("Controlling powdery mildew of roses using a plant extract and foliar fertilizers" Phytopathology, (Jun. 2001) vol. 91, No. 6, Supplement, pp. 101-102 (Year: 2001).*
Batish et al. "Eucalyptus essential oil as a natural pesticide", Forest Ecology and Management, vol. 256, Issue 12, Dec. 10, 2008, pp. 2166-2174. (Year: 2008).*
Djalma A. P. dos Santos et al. "Antiparasitic activities of acridone alkaloids from Swinglea glutinosa (Bl.) Merr.", J. Braz Chem. Soc . vol. 20, No. 4 Sao Paulo, 2009. (Year: 2009).*
Santos et al. "Antiparsitic activities of acridone alkaloids from Swinglea glutinosa" Journal of the Brazillian Chemical Society, vol. 20 No. 4 Sao Paulo 2009. (Year: 2009).*
Alvarez, E., et al., "Controlling powdery mildew of roses using a plant extract and foliar fertilizers," *Phytopathology* 91(6):S101, 2001/APS/MSA/SON Annual Meeting, MSA Abstracts, Salt Lake City, United States.
Braga, P.A.C., et al., "In vitro cytotoxicity activity on several cancer cell lines of acridone alkaloids and N-phenylethyl-benzamide derivatives from *Swinglea glutinosa* (Bl.) Merr.," *Natural Product Research* 21(1):47-55, Taylor & Francis, England (2007).
Bueno-Sanchez, J.G. et al., "Evaluación de la actividad antimicrobacetriana de algunas plantas aromáticas y medicinales que crecen en Colombia." Instituto Nacional de Salud, Grupo de Micobacterias, Bogotá, D.C., Centro Colombiano de Investigación en Tuberculosis CCITB, Colombia. Universidad Industrial de Santander, Bucaramanga, Centro de Investigación en Biomoléculas, CIBIMOL, CENIVAM2. Colombia. Jul. 23-28, 2008.
Dos Santos, D.A.P., et al., "Antiparasitic Activities of Acridone Alkaloids from *Swinglea glutinosa* (Bl.) Merr.," *J. Braz. Chem. Soc.* 20(4): 644-659, Sociedade Brasileira de Quimica, Brazil (Nov. 2009).
Purcaro, R., et al., "Algicide Constituents from *Swinglea glutinosa*," *J. Agric. Food. Chem.* 57:10632-10635, American Chemical Society, United States (Oct. 2009).
Weniger, B., et al., "Antiprotozoal activities of Colombian plants," *Journal of Ethnopharmacology* 78(2-3):193-200, Elsevier Science Ireland, Ltd., Ireland (2001).
Weniger, B., et al., "Bioactive Acridone Alkaloids from *Swinglea glutinosa*," *J. Nat. Prod.* 64(9):1221-1223, American Chemical Society and American Society of Pharmacognosy, United States (published online Sep. 8, 2001).
Final Office Action dated Jun. 8, 2011, in U.S. Appl. No. 12/860,896, filed Aug. 22, 2010, inventors Jimenez Martinez et al.
Non Final Office Action dated Nov. 12, 2010, in U.S. Appl. No. 12/860,896, filed Aug. 22, 2010, inventors Jimenez Martinez et al.
Final Office Action dated Jun. 8, 2011, in U.S. Appl. No. 12/891,841, filed Sep. 28, 2010, inventor Jimenez Martinez.
Non Final Office Action dated Dec. 15, 2010, in U.S. Appl. No. 12/891,841, filed Sep. 28, 2010, inventors Jimenez Martinez.
Non Final Office Action dated May 20, 2014, in U.S. Appl. No. 12/891,841, filed Sep. 28, 2010, inventor Jimenez Martinez.
Final Office Action dated Jul. 21, 2011, in U.S. Appl. No. 12/945,873, filed Nov. 14, 2010, inventor Jimenez Martinez.

(Continued)

*Primary Examiner* — Michael Barker
*Assistant Examiner* — Deborah A Davis
(74) *Attorney, Agent, or Firm* — Arent Fox LLP

(57) ABSTRACT

The invention of the present Application provides a standardized method to obtain an extract and the extract from leaves of *Swinglea glutinosa* , wherein the method yields an amount of extract that is about 60% the weight of the *Swinglea glutinosa* leaves.

7 Claims, No Drawings

(56) References Cited

OTHER PUBLICATIONS

Final Office Action dated Feb. 4, 2011, in U.S. Appl. No. 12/945,873, filed Nov. 14, 2010, inventor Jimenez Martinez.
Final Office Action dated Jun. 3, 2014, in U.S. Appl. No. 12/945,873, filed Nov. 14, 2010, inventor Jimenez Martinez.
European Patent Search Report completed Aug. 28, 2013, in European Application No. EP 10 77 4608, European Patent Office, Munich, Germany.
Non Final Office Action dated Nov. 15, 2010, in U.S. Appl. No. 12/466,801, filed May 15, 2009, inventor Jaime Toro Restrepo.
Final Office Action dated May 31, 2011, in U.S. Appl. No. 12/466,801, filed May 15, 2009, inventor Jaime Toro Restrepo.
Non Final Office Action dated May 12, 2014, in U.S. Appl. No. 12/466,801, filed May 15, 2009, inventor Jaime Toro Restrepo.
Final Office Action dated Sep. 16, 2014, in U.S. Appl. No. 12/466,801, filed May 15, 2009, inventor Jaime Toro Restrepo.
Non Final Office Action dated May 21, 2015, in U.S. Appl. No. 12/466,801, filed May 15, 2009, inventor Jaime Toro Restrepo.
Final Office Action dated Nov. 30, 2015, in U.S. Appl. No. 12/466,801, filed May 15, 2009, inventor Jaime Toro Restrepo.
Notice of Allowance dated Sep. 9, 2014, in U.S. Appl. No. 12/891,841, filed Sep. 28, 2010, inventor Jimenez Martinez.
Notice of Allowance dated Nov. 13, 2014 in U.S. Appl. No. 12/891,841, filed Sep. 28, 2010, inventor Jimenez Martinez.
Notice of Allowance dated Oct. 23, 2014, in U.S. Appl. No. 12/945,873, filed Nov. 14, 2010, inventor Jimenez Martinez.
Notice of Allowance dated Dec. 18, 2014, in U.S. Appl. No. 12/945,873, filed Nov. 14, 2010, inventor Jimenez Martinez.

* cited by examiner

METHOD OF PRODUCTION OF EXTRACT DERIVED FROM *SWINGLEA GLUTINOSA* LEAVES

CROSS-REFERENCE TO RELATED APPLICATIONS

This application is an continuation of U.S. patent application Ser. No. 12/466,801, filed May 15, 2009.

BACKGROUND OF THE INVENTION

1. Area of the Invention

The present invention is related to how to obtain an extract from *Swinglea glutinosa* leaves, and uses of the extract.

2. Description of Prior Art

*Swinglea glutinosa* derived compounds had been described to have multiple beneficial uses.

Weniger B. et al. discloses possible uses of acridone alkaloids from *Swinglea glutinosa* against *Plasmodium falciparum*, a protozoan which is the main cause of malaria disease (see Weniger B. et al., Bireactive Acridone Alkaloids from *Swinglea glutinosa*, J. Nat. Prod., 2001, 64(9):1221-3).

Braga P. A. C. et al. teaches the citotoxicity activity of derivatives of *Swinglea glutinosa* against cancer cell lines (see Braga P. A. C. et al., In Vitro Citotoxicity Activity on Several Cancer Cell Lines of Acridone Alkaloids and N-Phenylethyl-Benzamide derivatives from *Swinglea glutinosa*, Natural Product Research, 2007, 21(1):47-55).

Bueno-Sanchez J. G. et al. describes the potential of essential oils from *Swinglea glutinosa* against *Mycobacterium tuberculosis*, the tuberculosis causing agent (see Bueno-Sanchez J. G. et al., Assessment of Antimycobacterial Activity of Several Aromatic and Medicinal Plants that Grow in Colombia, Memoirs of VI National Encounter of Investigation in Infectious Diseases, Colombian Association of Infectology, 2008, page 96).

Unfortunately, there is no description in the prior art of a standardized method to obtain a good yield of a *Swinglea glutinosa* extract that can be used by itself or from which further beneficial derivatives compounds can be attained. The Invention of the present Application overcomes these prior art limitations.

SUMMARY OF THE INVENTION

The invention of the present Application provides a standardized method to obtain an extract and the extract from leaves of *Swinglea glutinosa*, wherein the method yields an amount of extract that is about 60% the weight of the *Swinglea glutinosa* leaves.

More specifically, the present Application invention provides an extract isolated from *Swinglea glutinosa* leaves, wherein said extract is obtained by a method comprising:
  A. Exposing bright dark green *Swinglea glutinosa* leaves in a dry environment, wherein said leaves are protected from direct sunlight, wherein the leaves are exposed to air flow;
  B. leaving the leaves in the environment described in A. until the leaves turn opaque green and the leaves are brittle;
  C. breaking up the leaves into small fragments;
  D. putting the *Swinglea glutinosa* leaf fragments in contact with a solvent at least once;
  E. repeat step D. until the solvent is enriched with substances derived from the leaf fragments; and,
  F. retiring the solvent to release the extract.

In one aspect, the extract, obtained by the method of the present Application invention, is used to kill fungi.

In another aspect, the extract, obtained by the method of the present Application invention, is used to kill insects and mites.

In one more aspect, the extract, obtained by the method of the present Application invention, is used to repel insects and mites.

In addition, the present Application invention provides a method for the production of an extract derived from *Swinglea glutinosa* plant, wherein said method comprises:
  A. Exposing bright dark green *Swinglea glutinosa* leaves in a dry environment, wherein said leaves are protected from direct sunlight, wherein the leaves are exposed to air flow;
  B. leaving the leaves in the environment described in A. until the leaves turn opaque green and the leaves are brittle;
  C. breaking up the leaves into small fragments;
  D. putting the *Swinglea glutinosa* leaf fragments in contact with a solvent at least once;
  E. repeat step D. until the solvent is enriched with substances derived from the leaf fragments; and,
  F. retiring the solvent to release the extract Objectives and advantages of the present Application invention will be more evident in the detailed description of the invention and the claims.

DETAILED DESCRIPTION OF THE INVENTION

The present invention provides an extract isolated from *Swinglea glutinosa* leaves, wherein said extract is obtained by a method comprising:
  A. Exposing bright dark green *Swinglea glutinosa* leaves in a dry environment, wherein said leaves are protected from direct sunlight, wherein the leaves are exposed to air flow;
  B. leaving the leaves in the environment described in A. until the leaves turn opaque green and the leaves are brittle;
  C. breaking up the leaves into small fragments;
  D. putting the *Swinglea glutinosa* leaf fragments in contact with a solvent at least once;
  E. repeat step D. until the solvent is enriched with substances derived from the leaf fragments; and,
  F. retiring the solvent to release the extract.

In one additional aspect of the method of the present invention, the leaves are protected in any way possible from direct exposure to sunlight.

In other aspect of the method of the present invention, the leaves that turn yellowish instead of opaque green are discarded. The period that the leaves take to turn into brittle leaves, and to turn from bright green leaves into opaque green leaves, depends on the optimal exposure to an air flow (aeration). Preferably, aeration occurs at 25° C., although changes in temperature may change the aeration period, e.g., small increases in temperature may shorten the aeration period.

In one more aspect of the method of the present invention, the leaves must not be broken into leaf fragments that are less than 0.05 mm, since smaller fragments would tend to become a single mass which will become a limitation for the optimal extraction with a solvent.

The leaf fragments are exposed to contact to the solvent by re-circulating the solvent throughout the bed where the leaf fragments are. However, the leaf fragments could be the ones moving throughout a container with solvent. In the case of the former, it is required that after each time the solvent is in contact with the leaf fragments, to evaporate the solvent into a separate space, keeping the extract obtained, then the vaporized solvent is re-liquefied and reused for a new cycle. There are as many cycles as necessary, until when there is not more extract obtained to keep. According to the method of the present invention, this is achieved when the remaining weight of the fragments leaf mass left is approximately 40% with respect to the weight of the leaf fragments before the first exposure to the solvent. In other words, the extract obtained constitutes approximately 60% of the initial leaf fragments weight In one aspect of the present invention, the solvent that can be used comprises ethanol, methanol, hexane, propanol, isopropanol, $CO_2$, acetone, water, ethyl-acetate, nitrile-acetate, toluene, tetrahydrofurane, Chloroform, dichloromethane, and others.

In one more aspect, the extract, obtained by the method of the present Application invention, is used to kill fungi.

In another aspect, the extract, obtained by the method of the present Application invention, is used to kill insects and mites.

In one more aspect, the extract, obtained by the method of the present Application invention, is used to repel insects and mites.

In addition, the present Application invention provides a method for the production of an extract derived from *Swinglea glutinosa* plant, wherein said method comprises:
  A. Exposing bright dark green *Swinglea glutinosa* leaves in a dry environment, wherein said leaves are protected from direct sunlight, wherein the leaves are exposed to air flow;
  B. leaving the leaves in the environment described in A. until the leaves turn opaque green and the leaves are brittle;
  C. breaking up the leaves into small fragments;
  D. putting the *Swinglea glutinosa* leaf fragments in contact with a solvent at least once;
  E. repeat step D. until the solvent is enriched with substances derived from the leaf fragments; and,
  F. Retiring the solvent to release the extract In one aspect of the present invention, the extract of can be used to kill fungi, wherein susceptible fungi comprises:
*Sphaerotheca pannosa*
*Botritys* sp.
*Fusarium* sp.
*Colletotrichum* sp.
*Uncinola necator*
*Variola* sp.
*Peronospora* sp.
*Puccinia* sp.
*Cladosporium* sp./*Hetesroporium* sp.,
and others.

In another aspect of the present invention, the extract can be used to kill insects and mites, wherein susceptible insects and mites comprise:
*Liriomyza* sp
*Tetranichus* sp.
*Boophilus microplus,*
and others In one additional aspect of the present invention, the extract can be used to repel insects and mites, wherein susceptible insects and mites comprise:
*Liriomyza* sp
*Tetranichus* sp.
*Boophilus microplus,*
and others The extract of the present invention can be combined with camphor and oils that have been described to kill fungi, kill and or repel insects and mites, wherein the oils would enhance the effects of the *Swinglea glutinosa* extract against fungi, insects, and mites, and wherein the oils can be derived from garlic, orange, lemon, lime, *Cymbopogon* sp., *Eugenia caryophyllata, Eucalyptus* sp., *Melaleuca alternifolia, Citrus simensis,* other *citrus* sp., cinnamon, and others Objectives and advantages of the present Application invention will be more evident in the detailed description of the invention and the claims.

EXAMPLES

Branches with dark bright green leaves of *Swinglea glutinosa* tree were collected and put under a roof at approximately 25° C., in a place where there was a natural air flow. The branches with leaves were periodically moved to guarantee exposition all leaves to the air flow. After approximately three days, the leaves that were dry and turned opaque green were collected from the branches, and said dry opaque green leaves were broken into fragments of no more than 0.05 mm with a blade mill. About 30 Kilograms of leaf fragments were put into a steel sieve with 0.05 mm net-apertures. The container holding the steel sieve holding the leaf fragments was filled with a mix of 320 liters ethanol and 70 liters of water for about 45 minutes. The ethanol-water mix was withdrawn and the ethanol-water was vaporized by heating. The remaining extract was kept, and the vaporized ethanol-water was turned into liquid again in a separate closed spaced with a condenser. The ethanol-water mix was reused to fill the container holding the steel sieve with leaf fragments for six more times, each time from 25 minutes to 35 minutes. The final amount of extract obtained was about 18 liters, wherein said extract was a dark green viscous material.

A solution of 2 ml Extract/Liter of water was prepared and used for the following experiment:

An isolated strain of a pathogenic fungus was propagated in an adequate culture medium for the strain. Then, a suspension on water was prepared at a concentration of $1 \times 10^6$ spores/ml. A plate with the culture medium only and a plate with the cultured medium prepared with the 2 ml Extract/Liter of water solution, were prepared. Both plates were bathed with 20 µl of the suspension with spores.

After incubation of the plates for 12 days at room temperature the percentage of inhibition for each fungus was measured with the following results:

| | |
|---|---|
| *Fusarium oxysporum* | 72.20% |
| *Botrytis cinerea* | 80.70% |
| *Mycosphaerella fijiensis* | 68.40% |
| *Colletotrichum* sp. | 90.44% |

For *Sphaerotheca pannosa* a spore suspension was applied to leaves of healthy rose plants bathed with the 2 ml Extract/Liter of water solution, and to leaves of un-bathed healthy rose plants. Then the leaves of both rose plants were observed for formation of fungi pustules after 15 days. There was a 65.7% less formation of pustules in the leaves of rose plants bathed with the 2 ml Extract/Liter of water solution.

With respect to *Liriomyza* sp. a repellence test was made by comparing bathed leaves of bean plants with the 2 ml Extract/Liter of water solution and un-bathed leaves of bean plants. The plants with bathed and un-bathed leaves were put inside a cage with *Liriomyza* sp. After 24 hours points of disease caused by *Liriomyza* sp. in leaves of both plants were compared. The plants with leaves bathed with the 2 ml of Extract/Liter of water solution presented 75.3% less points of disease than the plants with un-bathed leaves.

With respect to *Tetranichus* sp. a repellence test was made by comparing 5 mm discs cut from leaves of bean plants, wherein 5 mm leaf discs that were bathed with the 2 ml of Extract/Liter of water solution were compared against un-bathed 5 mm leaf discs, and wherein a 2 mm un-bathed leave disc with a *Tetranichus* sp. mites was put on top of both 5 mm leaf discs. After 24 hours there were 78.4% less *Tetranichus* sp. mites on top of the 5 mm leaf discs bathed with the 2 ml of Extract/Liter of water solution than in the un-bathed 5 mm leaf discs.

With respect to *Boophilus microplus* (ticks) a 5 ml of Extract/Liter of water solution was used in a mortality experiment, wherein adult regurgitated ticks that were bathed with the 5 ml of Extract/Liter of water solution were compared against un-bathed ticks. Both, the bathed ticks and the un-bathed ticks were put in a Petri dish and observed. After three days, there was 75% more deaths among the ticks bathed with the 5 ml of Extract/Liter of water solution than among the un-bathed ticks.

The invention claimed is:

1. A method to kill fungi comprising contacting a fungus with an effective amount of a fungicide composition, wherein the composition comprises an extract from *Swinglea glutinosa* leaves prepared by extraction with a water:organic solvent mixture, and wherein the extract from *Swinglea glutinosa* leaves does not contain acridones.

2. The method according to claim 1, wherein the fungus belongs to the genus *Sphaerotheca, Botrytis, Fusarium, Colletotrichum, Uncinola, Variola, Peronospora, Puccinia, Cladosporium, Mycosphaerella,* or *Heterosporium.*

3. The method according to claim 2, wherein the fungus is *Sphaerotheca pannosa, Botrytis cinerea, Fusarium oxysporum, Uncinola necator,* or *Mycosphaerella fifiensis.*

4. The method according to claim 1, wherein the fungicide composition further comprises at least one additional plant extract.

5. The method according to claim 4, wherein the at least one additional plant extract is selected from camphor, garlic oil, orange oil, lemon oil, lime oil, *Cymbopogon* sp. oil, *Eugenia caryophyllata* oil, *Eucalyptus* sp. oil, *Melaleuca alternifolia* oil, *Citrus sinensis* oil, *Citrus* sp. oil, cinnamon oil, and combinations thereof.

6. The method according to claim 1, wherein the organic solvent is selected from the group consisting of ethanol, methanol, hexane, propanol, isopropanol, acetone, ethyl-acetate, nitrile-acetate, toluene, tetrahydrofurane, chloroform, dichloromethane, and combinations thereof.

7. The method according to claim 1, wherein the organic solvent is ethanol.

* * * * *

UNITED STATES PATENT AND TRADEMARK OFFICE
CERTIFICATE OF CORRECTION

PATENT NO. : 10,470,467 B2
APPLICATION NO. : 15/056303
DATED : November 12, 2019
INVENTOR(S) : Jaime Toro Restrepo et al.

Page 1 of 1

It is certified that error appears in the above-identified patent and that said Letters Patent is hereby corrected as shown below:

On the Title Page

Item (72), listing the inventors, correct Sandra Patricia Zapata Rojas to --Sandra Patricia Zapata Porras, Medellin (CO)--

Signed and Sealed this
Seventh Day of April, 2020

Andrei Iancu
*Director of the United States Patent and Trademark Office*